(12) United States Patent
Yanagihara et al.

(10) Patent No.: US 7,336,991 B2
(45) Date of Patent: Feb. 26, 2008

(54) MULTI-CHANNEL BIOLOGICAL SIGNAL TELEMETRY SYSTEMS

(75) Inventors: Kazuteru Yanagihara, Tokyo (JP); Takahisa Ishikawa, Tokyo (JP); Kaoru Imajo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 503 days.

(21) Appl. No.: 10/948,261

(22) Filed: Sep. 24, 2004

(65) Prior Publication Data
US 2005/0085872 A1    Apr. 21, 2005

(30) Foreign Application Priority Data
Sep. 26, 2003  (JP) .......................... P2003-334751

(51) Int. Cl.
*A61B 5/04* (2006.01)

(52) U.S. Cl. .................... 600/544; 128/903; 607/16; 607/32

(58) Field of Classification Search ........... 600/544, 600/485–503, 300, 529–542, 345–350, 60; 340/539.12, 3.21, 3.3, 3.31, 870.28, 636.1, 340/636.19; 375/240; 607/60, 32, 16; 455/574, 455/127.5, 343.1, 343.2, 343.5; 128/903, 128/905
See application file for complete search history.

(56) References Cited

U.S. PATENT DOCUMENTS

| | | | | |
|---|---|---|---|---|
| 4,958,645 | A * | 9/1990 | Cadell et al. ............... | 600/484 |
| 5,748,103 | A * | 5/1998 | Flach et al. ............. | 340/870.07 |
| 5,767,791 | A * | 6/1998 | Stoop et al. ........... | 340/870.11 |
| 5,924,979 | A * | 7/1999 | Swedlow et al. ........... | 600/300 |
| 5,963,650 | A * | 10/1999 | Simionescu et al. .......... | 705/63 |
| 6,213,942 | B1 * | 4/2001 | Flach et al. ................. | 600/300 |
| 6,271,767 | B1 * | 8/2001 | Frye et al. ............... | 340/853.2 |
| 6,456,887 | B1 * | 9/2002 | Dudding et al. .............. | 607/60 |
| 6,473,607 | B1 * | 10/2002 | Shohara et al. .......... | 455/343.1 |
| 6,496,705 | B1 * | 12/2002 | Ng et al. .................... | 455/502 |
| 6,734,802 | B2 * | 5/2004 | Halleck et al. ............. | 340/669 |
| 7,007,177 | B2 * | 2/2006 | Cannon et al. ............. | 713/300 |
| 2004/0113771 | A1* | 6/2004 | Ozaki et al. ........... | 340/539.12 |

(Continued)

FOREIGN PATENT DOCUMENTS

JP        6-105816 A        4/1994

(Continued)

*Primary Examiner*—Charles A. Marmor, II
*Assistant Examiner*—Anita Saidi
(74) *Attorney, Agent, or Firm*—Sughrue Mion, PLLC

(57) ABSTRACT

A system for performing telemetry of multi-channel biological signals obtained from electrodes attached to a subject, is provided with a transmitter and a receiver. In the transmitter, a converter converts the multi-channel biological signals to digital data, and a storage stores the digital data. In the transmitter, a first transceiver is operable to transmit a prescribed amount of the digital data stored in the storage, and a battery is operable to supply a battery voltage to the first transceiver. In the transmitter, a switch places the battery in either a first state where the battery voltage is supplied to the first transceiver or a second state where the battery voltage is not supplied to the first transceiver, so that the first transceiver intermittently transmits the digital data. In the receiver, a second transceiver is operable to receive the digital data transmitted from the first transceiver. The received digital data is to be reproduced multi-channel biological signals at an output device.

3 Claims, 4 Drawing Sheets

U.S. PATENT DOCUMENTS

| | | | |
|---|---|---|---|
| 2004/0116786 A1* | 6/2004 | Iijima et al. | 600/301 |
| 2005/0118981 A1* | 6/2005 | Laroia et al. | 455/343.3 |
| 2005/0164637 A1* | 7/2005 | Pattabiraman et al. | 455/41.2 |
| 2006/0125623 A1* | 6/2006 | Appelt et al. | 340/521 |

FOREIGN PATENT DOCUMENTS

| | | | |
|---|---|---|---|
| JP | 8-71050 A | 3/1996 |
| JP | 2827969 B2 | 9/1998 |
| JP | 10-262943 A | 10/1998 |
| JP | 11-28196 A | 2/1999 |
| JP | 3125077 B2 | 11/2000 |
| JP | 2003-38453 A | 2/2003 |

* cited by examiner

MULTI-CHANNEL BIOLOGICAL SIGNAL TELEMETRY SYSTEMS

BACKGROUND OF THE INVENTION

The present invention relates to a multi-channel biological signal telemetry system for measuring or monitoring biological signals, such as electroencephalograms, which are led from a human scalp or the surface of the cerebral cortex as feeble potential variations (of several to hundreds of µV) having frequency components superposed thereon, an electrocardiogram, an electromyogram, respiratory waveforms, $SpO_2$, or the like.

Since the physical and/or mental state of a person can be determined by frequencies of electroencephalograms obtained by the person, a system for controlling equipment, such as a reclining apparatus, by utilization of electroencephalograms has hitherto been developed. For instance, Japanese Patent Publication No. 8-71050A discloses a system capable of creating a comfortable environment by controlling an equipment on the basis of not only information about electroencephalograms sampled at the present time, but also the difference between the preset desired physical and/or mental state and the present physical and/or mental state. This system is configured such that a detected electroencephalogram is transmitted in a wireless manner, and frequencies and intensities of the received electroencephalogram is analyzed to evaluate comfortableness of the environment.

Because human electroencephalograms are very feeble electrical signals and include random waveforms called brain noise, difficulty is encountered in determining an S/N ratio and sampling electroencephalogram data. For this reason, Japanese Patent Publication No. 10-262943A teaches that: electroencephalogram data sets are detected from a plurality of points on a surface of a scalp; prescribed frequency components are extracted respectively from the thus-detected plurality of sets of electroencephalogram data; frequency band differential data pertaining to respective frequency ranges is determined after having applied common temporal weighting to the prescribed frequency components data sets; and an electroencephalogram (EEG) topography map is displayed on the basis of the frequency band differential data.

More specifically, under the electroencephalogram measurement method disclosed in this publication, an apparatus is configured such that electroencephalogram data of respective channels detected by cap-shaped electrodes are amplified by a multi-channel amplifier and converted into digital data by an A/D converter; prescribed frequency components are extracted from the thus-converted digital data in a digital band pass filter section; data of respective channels are subjected to common temporal weighting in a window function section; the thus-temporal-weighted data are converted into data in a frequency range by a frequency analysis processing section; a frequency band differential operation section determines frequency band differential data for each data frequency range of each channel; and an indicator displays an EEG topography map based on mapping data formed from the frequency band differential data.

Furthermore, Japanese Patent No. 2827969 discloses a medical telemetry system of digital modulation scheme and a medical telemetry apparatus. Particularly, the medical telemetry apparatus does not have any biological signal measurement section, but receives biological signal data detected and digitized by another piece of medical equipment by way of a dedicated line, and transmits the thus-received data in a wireless manner.

This medical telemetry system comprises: i) a bedside monitor which measures biological signals of a patient and outputs measurement data resulting from digitization of the thus-measured data; ii) a medical telemetry apparatus which includes frequency setting means for modifying and setting a transmission frequency; receives the measured data by way of a dedicated line; adds to the thus-received data a sender identification code, which is to become a radio channel code indicating a transmission frequency set by the frequency setting means, to thus acquire transmission data; and sends a modulated wave resulting from digital modulation of a carrier wave having a transmission frequency set by the transmission data through radio transmission; and iii) a central monitor which receives the modulated wave; demodulates the received modulated data to thereby obtain the transmission data; compares a receiver identification code with the sender identification code in the transmission data; and displays and records measurement data in the transmission data only when these identification codes coincide with each other.

Further, Japanese Patent No. 3125077 discloses a portable telemetry apparatus capable of preventing consumption of a battery in the event of abnormal placement of electrodes. The biological signal telemetry apparatus is configured so as to be carried by a patient; is supplied with a direct current power source from a built-in battery; and transmits biological signal waveforms led by the electrodes placed on the subject, by a radio signal from a transmission circuit. This biological signal telemetry apparatus comprises an electrode anomaly detection circuit which detects the state of the electrodes placed on the subject and outputs an electrode detachment signal for a period during which the electrodes are placed anomaly; and a switch circuit which interrupts supply of the direct current power source to the transmission circuit during a period in which the switch circuit is receiving the electrode detachment signal from the electrode anomaly detection circuit.

A conventional electroencephalogram telemetry apparatus, or the like, employs a medical telemetry band of 400 MHz, at which a data transmission speed is quite low. Accordingly, great difficulty is encountered in transmitting electroencephalogram data, which require high resolution and high sampling per channel, on 32 channels or more.

Further, a general transceiver consumes a considerable amount of current, regardless of an operating state, only when the power of the transceiver is active. Therefore, the current consumed by the transceiver (i.e., consumption of a battery) becomes dominant over the current consumed by an amplifier circuit (consumption of the battery).

Further, the greater the number of, e.g., amplifier circuits, are additionally provided to implement multi-channeling during transmission of electroencephalogram data, the greater the consumed current increases. Therefore, in an attempt to embody a portable multi-channel telemetry apparatus which is operated by utilization of a battery as a power source, an operable time becomes fairly shorter. For instance, long-term operation of 24 hours or longer is highly difficult.

As described above, a system configuration of a related-art electroencephalogram telemetry apparatus has failed to implement a portable multi-channel electroencephalogram telemetry system of 32 channels or more capable of performing battery-powered operation for 24 hours or longer.

SUMMARY OF THE INVENTION

It is therefore an object of the invention to provide a multi-channel biological signal telemetry system which enables continuous, long-term measurement of multi-channel biological signal information even when a patient on the move carries a biological signal information transmitter.

It is also an object of the invention to provide a multi-channel biological signal telemetry system capable of increasing the amount of information by multi-channeling electroencephalogram data, and enabling continuous measurement over a long time period, in order to realize simple, flexible and accurate analysis in connection with monitoring of expression of pathological signs of diseases such as epilepsy or polysomnography (hereinafter referred to as "PSG") testing or the like, thereby enabling effective detection of a part of the brain causing epileptic episodes, abnormal electroencephalograms, or the like, and treatment thereof.

In order to achieve the above objects, according to the invention, there is provided a system for performing telemetry of multi-channel biological signals obtained from electrodes attached to a subject, comprising:

a transmitter, comprising:
- a converter, which converts the multi-channel biological signals to digital data;
- a storage, which stores the digital data;
- a first transceiver, operable to transmit a prescribed amount of the digital data stored in the storage;
- a battery, operable to supply a battery voltage to the first transceiver; and
- a switch, which places the battery in either a first state where the battery voltage is supplied to the first transceiver or a second state where the battery voltage is not supplied to the first transceiver, so that the first transceiver intermittently transmits the digital data; and a receiver, comprising a second transceiver operable to receive the digital data transmitted from the first transceiver, the received digital data being to be reproduced multi-channel biological signals at an output device.

With the above configuration, power consumption of the battery for the first transceiver can be suppressed. Accordingly, there is enabled continuous, long-term measurement of multi-channel biological signal information in an unconstrained manner, which has been conventionally considered to be difficult, and flexible and more accurate analysis and diagnosis can be conducted in a simple and convenient manner for monitoring, examining, and the like expression of various pathological signs of diseases. As a result, discovery of a disease and treatment thereof can be effectively attained.

Preferably, the transmitter further comprises a detector which detects the battery voltage. The first transceiver is operable to transmit battery information indicating the detected battery voltage together with the digital data, and the second transceiver is operable to receive the battery information. The receiver further comprises a timing information provider, which prepares timing information defining a timing for placing the battery in the first state, on the basis of the battery information received by the second transceiver. The second transceiver is operable to transmit the timing information and the first transceiver is operable to receive the timing information. The switch places the battery in the second state after the digital data and the battery information are transmitted, and places the battery in the first state at the timing on the basis of the timing information received by the first transceiver.

Here, it is preferable that the timing information provider prepares the timing information so as to delay the timing in a case where the battery information indicates that the detected battery voltage becomes lower than a threshold value.

With the above configurations, the timing for activating or deactivating the battery for the first transceiver can be appropriately determined in accordance with the residual amount of the battery.

Preferably, the biological signal includes electroencephalograms.

In this case, flexible and accurate analysis and diagnosis can be conducted in a simple and convenient manner in connection with PSG testing, monitoring of expression of various pathological signs of diseases such as epilepsy, or the like.

Preferably, the digital data is transmitted with a frequency band defined as an Industrial Scientific and Medical Application band.

In this case, since a transmission speed of the digital data by way of wireless transmission is increased, a period until completion of the data transmission is shortened. Accordingly, a time period during which the battery for the transceiver is activated can be further shortened while prolonging a time period during which the battery is deactivated, whereby the operable time of the battery is prolonged.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

Embodiments of a multi-channel biological signal telemetry system according to the present invention will be described hereinbelow in detail by reference to the accompanying drawings.

Figure 1:
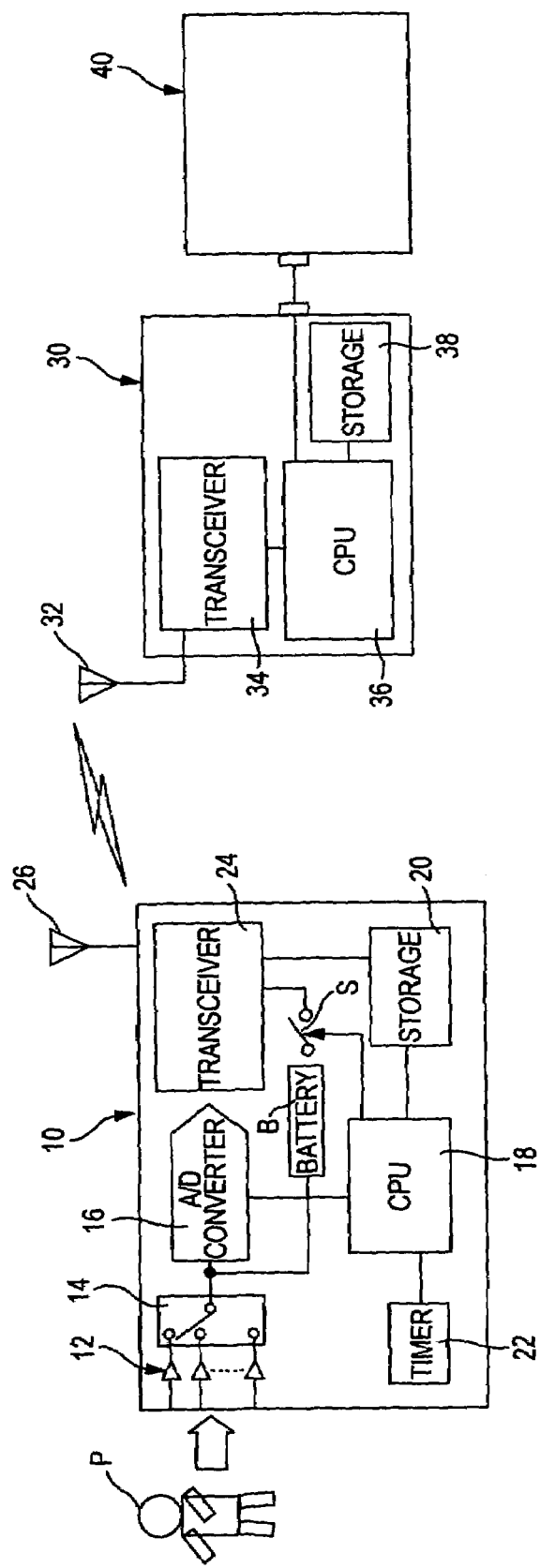
FIG. 1 is a schematic block diagram of a multi-channel biological signal (electroencephalogram) telemetry system according to one embodiment of the invention.

FIG. 1 shows a multi-channel electroencephalogram telemetry system according to one embodiment of the multi-channel biological signal telemetry system of the invention. The multi-channel electroencephalogram telemetry system comprises a transmitter 10, a receiver 30, and an electroencephalograph 40.

The transmitter 10 comprises a multi-channel amplifier 12, a multiplexer 14, an A/D converter 16, a CPU 18, a storage 20, a timer 22, a transceiver 24, an antenna 26, a battery B for activating the transceiver 24, and a switch S which switches between activation and deactivation of the battery B. The multi-channel amplifier 12 amplifies respective electroencephalogram signals detected from a plurality of electrodes (unillustrated) attached on a head of a patient P upon input thereof.

The receiver 30 comprises an antenna 32, a transceiver 34, a CPU 36, and a storage 38. The electroencephalograph 40 is externally connected to the receiver 30 by way of the CPU 36.

The transmitter 10 is configured as follows. The multi-channel amplifier 12 obtains multi-channel electroencephalogram signals, and the thus-obtained signals are converted from analog signals into digital signals by the A/D converter 16 after passing through the multiplexer 14, whereby multi-channel electroencephalogram data are obtained. The thus-obtained multi-channel electroencephalogram data are sequentially stored in the storage 20 by way of the CPU 18. When a prescribed amount of multi-channel electroencephalogram data is accumulated in the storage 20, the switch S of the battery B serving as a power source of the transceiver 24 is activated at a timing which has been preset by the timer 22 by way of the CPU 18, whereby the transceiver 24 is activated. Accordingly, the prescribed amount of multi-channel electroencephalogram data accumulated in the storage 20 is transmitted from the transceiver 24 to the receiver 30 by way of the antenna 26.

On the other hand, the receiver 30 is configured as follows. The transceiver 34 receives the prescribed amount of multi-channel electroencephalogram data transmitted from the transmitter 10 by way of the antenna 32. The thus-received data are then stored in the storage 38 by way of the CPU 36. The prescribed amount of electroencephalogram data received by the transceiver 34 is read directly or from the storage 38 by way of the CPU 36, and outputted to the electroencephalograph 40 to be displayed as electroencephalograms.

In this embodiment, Industrial Scientific and Medical Application Band (ISM band), which employs a frequency of, e.g., 2.4 GHz, is used for the electroencephalogram data transmission, thereby enabling high-speed and large-amount data transmission.

The battery B for the transceiver 24 is deactivated by way of the switch S at a timing prescribed in the timer 22. That is, the battery B is intermittently deactivated so as to prolong the operable time. As a result, long-term usage of the transmitter 10 is enabled.

More specifically, a detector is provided in the CPU 18 to detect present voltage information of the battery B or the like, so that the battery voltage information is transmitted with the multi-channel electroencephalogram data. Subsequently, the transmitter 10 issues an inquiry for a timing of starting a next transmission of the multi-channel electroencephalogram data (i.e., a timing of reactivating the battery B for the transceiver 24) with respect to the receiver 30.

On the other hand, a timing provider is provided in the CPU 36 to determine the timing of restarting the data transmission (reactivating the battery B) on the basis of the received battery voltage information. For instance, in a case where the battery voltage information indicates that the battery voltage becomes lower than a prescribed value, timing information is prepared so as to prolong the deactivated time period of the battery B for the transceiver 24. The timing information is transmitted as a reply from the receiver 30 to the transmitter 10 to be set in the timer 22.

Figure 2:
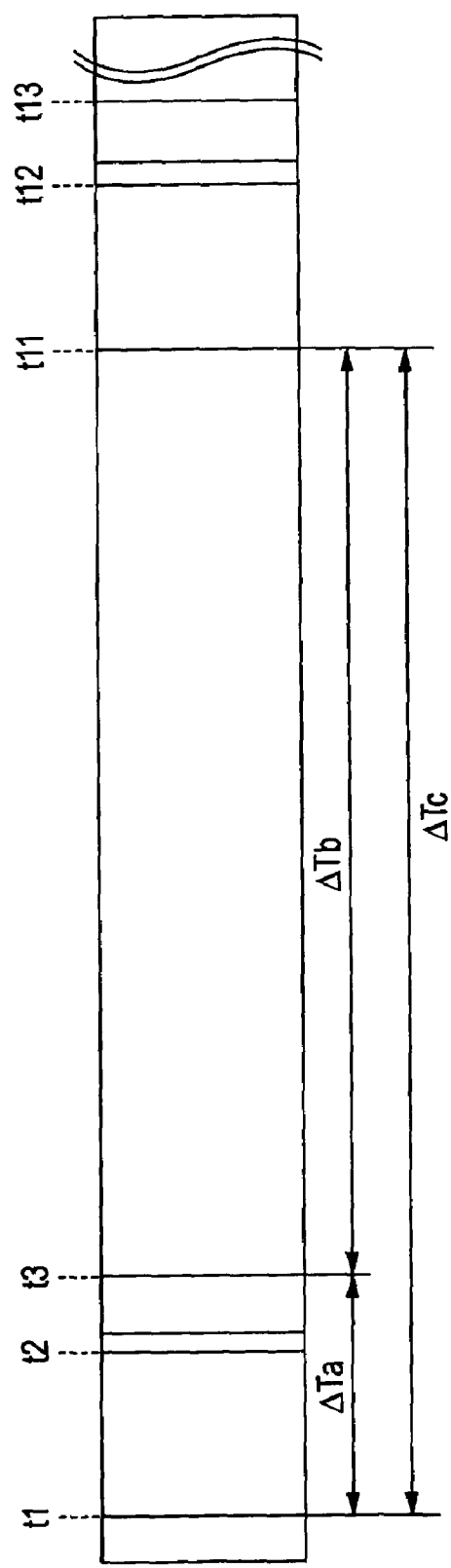
FIG. 2 is a timing chart showing operations of a transmitter in the telemetry system of FIG. 1.

FIG. 2 schematically shows the above operations in the transmitter 10. At a timing t1 for activating the battery B, the transceiver 24 is activated to start the transmission of the prescribed amount of multi-channel electroencephalogram data accumulated in the storage 20 together with the battery voltage information. The transmission is continued until a prescribed timing t2. After completion of the data transmission, the timing information for the next data transmission which has been prepared by the receiver 30 is obtained until a prescribed timing t3. At the timing t3, the battery B is deactivated. Therefore, a time period $\Delta Ta$ during which the transceiver 24 is activated is defined as a time period between the timings t1 and t3.

Meanwhile, based on the timing information obtained in the transmitter 10, there is set a timing t11 for reactivating the transceiver 24 and restarting transmission of the next set of multi-channel electroencephalogram data and the battery voltage information. That is, a time period $\Delta Tb$ during which the battery B for the transceiver 24 is deactivated is determined in accordance with timing information. Under the normal condition, the data transmission is intermittently executed at a prescribed constant interval $\Delta Tc$. In a case where the battery voltage information indicates that the battery voltage becomes lower than the prescribed value, the time period $\Delta Tb$ ($\Delta Tc$) is prolonged by the timing information to suppress the power consumption of the battery B.

Figure 3:
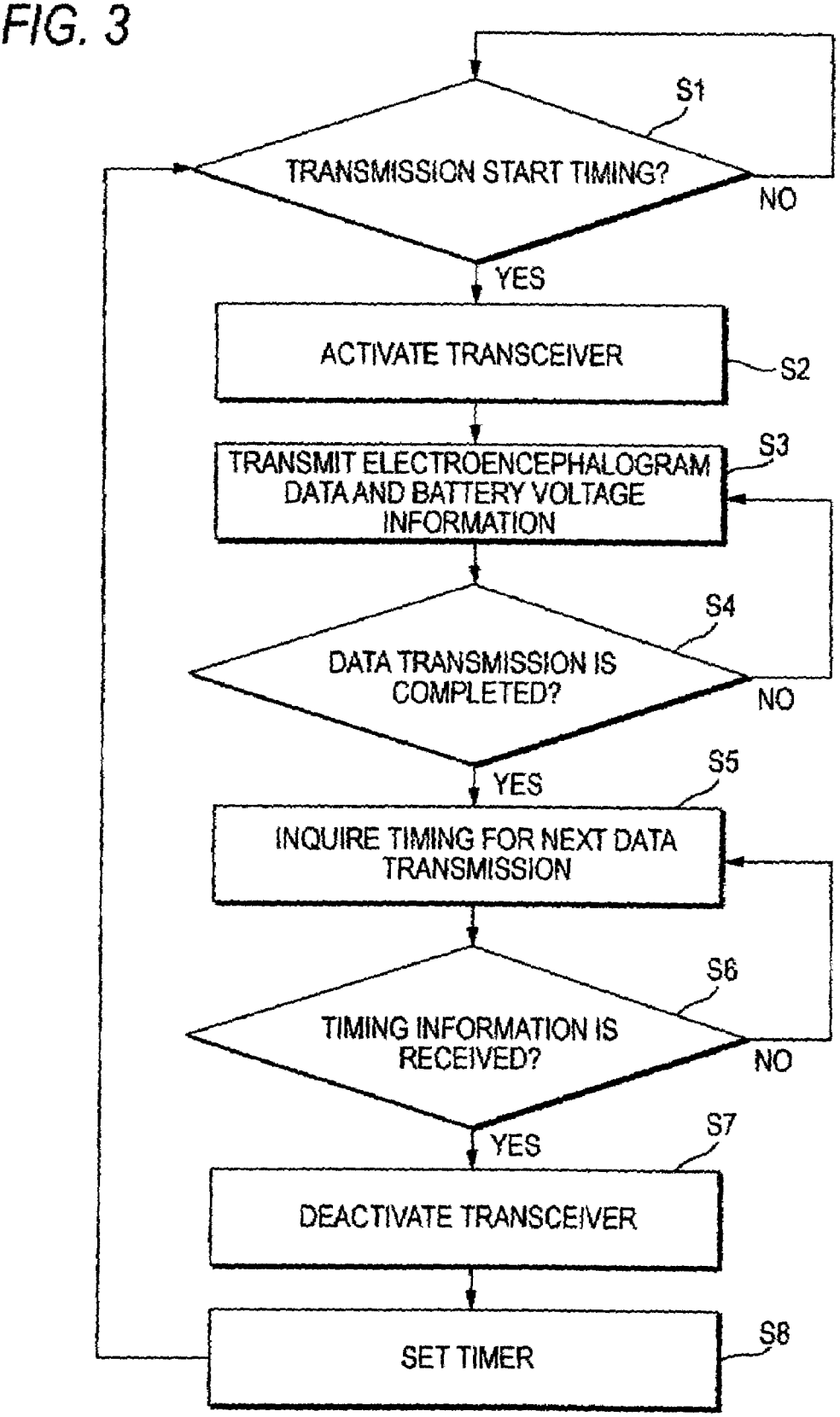
FIG. 3 is a flow chart showing operations executed in the transmitter of FIG. 1.

FIG. 3 shows an operation flow chart at the transmitter 10. First, a determination is made as to whether the prescribed timing t1 for starting the data transmission comes (step S1). When the timing t1 comes, the battery B is activated to accordingly activate the transceiver 24 (step S2), so that a prescribed amount of multi-channel electroencephalogram data accumulated in the storage 20 and the battery voltage information is transmitted to the receiver 30 (step S3). Next, a determination is made as to whether or not the transmission of the data and the information is completed (step S4). When the transmission is completed, an inquiry for the timing information of next transmission is sent to the receiver 30 (step S5). Subsequently, a determination is made as to whether or not the prescribed timing information sent by the receiver 30 is obtained (step S6). When the timing information is obtained, the battery B is deactivated and the transceiver 24 is brought into an inactive state (step S7). A timing t11 for starting the next transmission is set in the timer 22 on the basis of the thus-obtained timing information (step S8). Operations of the above-mentioned step S1 through step S8 are then repeated from step S1.

Figure 4:
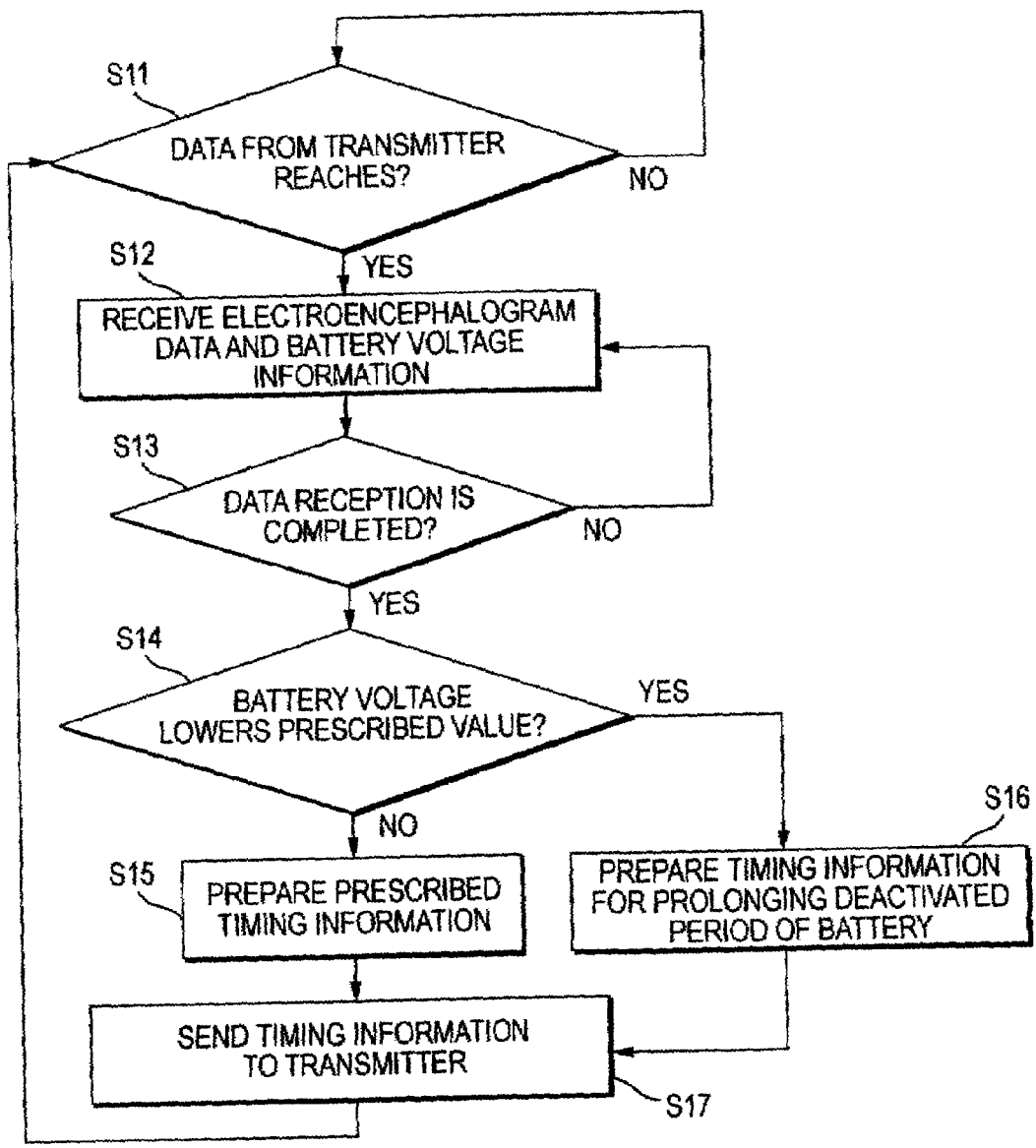
FIG. 4 is a flow chart showing operations executed in a receiver in the telemetry system of FIG. 1.

FIG. 4 shows an operation flow chart at the receiver 30. First, a determination is made as to whether or not the multi-channel electroencephalogram data and the battery voltage information from the transmitter 10 are recognized by the transceiver 34 (step S11). When they are recognized, the multi-channel electroencephalogram data and the battery voltage information are obtained (step S12). Next, a determination is made as to whether or not the receipt of the multi-channel electroencephalogram data and the battery voltage information is completed (step S13). When receiving operation is completed, a determination is made as to whether or not the battery voltage has become lower than a prescribed threshold value, on the basis of the battery voltage information (step S14). When the battery voltage is not lower than the threshold value, timing information is prepared in a way indicating that no change is made for the timing t11 for starting the next transmission by the transmitter 10 (step S15). The thus-prepared timing information is sent to the transmitter 10 (step S17). On the other hand, when the battery voltage is lower than the threshold value, timing information for delaying the timing t11 is prepared (step S16). The thus-prepared timing information is sent to the transmitter 10 (step S17). Operations of the above-mentioned step S11 through step S17 are then repeated from step S11.

The present invention is not limited to the multi-channel electroencephalogram telemetry system as mentioned in the above. For instance, the invention can be applied widely as a telemetry system for biological signals of an electrocardiogram, electromyogram, respiratory waveforms, $SpO_2$, or the like, and can be modified in various manners without departing from the scope of the invention.

What is claimed is:

1. A system for performing telemetry of multi-channel biological signals obtained from electrodes attached to a subject, the system comprising:

a transmitter, comprising:

a converter, which converts the multi-channel biological signals to digital data;

a storage, which stores the digital data;

a first transceiver, operable to transmit a prescribed amount of the digital data stored in the storage;

a battery, operable to supply a battery voltage to the first transceiver; and a switch, which places the battery in either a first state where the battery voltage is supplied to the first transceiver or a second state where the battery voltage is not supplied to the first transceiver, so that the first transceiver intermittently transmits the digital data; and a receiver, comprising a second transceiver operable to receive the digital data transmitted from the first transceiver, the received digital data operable to be reproduced as multi-channel biological signals at an output device, wherein the transmitter further comprises a detector which detects the battery voltage;

the first transceiver is operable to transmit battery information indicating the detected battery voltage together with the digital data, and the second transceiver is operable to receive the battery information;

the receiver further comprises a timing information provider, which prepares timing information defining a timing for placing the battery in the first state, on the basis of the battery information received by the second transceiver;

the second transceiver is operable to transmit the timing information and the first transceiver is operable to receive the timing information; and the switch places the battery in the second state after the digital data and the battery information are transmitted, and places the battery in the first state at the timing on the basis of the timing information received by the first transceiver.

2. The system as set forth in claim 1, wherein the timing information provider prepares the timing information so as to delay the timing in a case where the battery information indicates that the detected battery voltage becomes lower than a threshold value.

3. The system as set forth in claim 1, wherein the biological signal includes electroencephalograms.

* * * * *